(12) United States Patent
Scherkowski (10) Patent No.: US 10,722,697 B2
(45) Date of Patent: Jul. 28, 2020

(54) SKIN PIERCING TOOL FOR LOCALLY PUNCTURING A HUMAN OR AN ANIMAL SKIN AND HAND-HELD DEVICE

(71) Applicant: MT.DERM GmbH, Berlin (DE)

(72) Inventor: Dirk Scherkowski, Berlin (DE)

(73) Assignee: MT DERM GmbH, Berlin (DE)

( * ) Notice: Subject to any disclaimer, the term of this patent is extended or adjusted under 35 U.S.C. 154(b) by 297 days.

(21) Appl. No.: 15/059,798

(22) Filed: Mar. 3, 2016

(65) Prior Publication Data

US 2016/0256674 A1 Sep. 8, 2016

(30) Foreign Application Priority Data

Mar. 6, 2015 (EP) ..................... 15158066

(51) Int. Cl.
*A61M 37/00* (2006.01)
*A61B 5/15* (2006.01)
(Continued)

(52) U.S. Cl.
CPC ... *A61M 37/0015* (2013.01); *A61B 5/150022* (2013.01); *A61B 5/15105* (2013.01); *A61B 5/15142* (2013.01); *A61B 5/150412* (2013.01); *A61B 5/150503* (2013.01); *A61B 5/150526* (2013.01); *A61D 7/00* (2013.01); *A61M 5/178* (2013.01); *A61M 37/0076* (2013.01); *A61B 17/205* (2013.01); *A61M 2037/0023* (2013.01); *A61M 2037/0046* (2013.01); *A61M 2250/00* (2013.01)

(58) Field of Classification Search
CPC .......... A61M 37/0076; A61M 37/0015; A61M 2037/0023; A61M 2037/0046; A61B 5/150503; A61B 5/150526; A61B 5/15105; A61B 5/150412; A61B 5/15142; A61B 18/1487; A61B 18/802; A61B 18/1492
See application file for complete search history.

(56) References Cited

U.S. PATENT DOCUMENTS 6,090,790 A * 7/2000 Eriksson .............. A61K 9/0021
435/440
2005/0065483 A1 3/2005 Nakao
(Continued)

FOREIGN PATENT DOCUMENTS

EP 1 576 982 9/2005
EP 1 872 823 1/2008
(Continued)

*Primary Examiner* — Kevin C Sirmons
*Assistant Examiner* — Tezita Z Watts
(74) *Attorney, Agent, or Firm* — Leason Ellis LLP (57) ABSTRACT

The disclosure relates to a skin piercing tool for locally puncturing a human or an animal skin, comprising a piercing needle, which is embodied as solid needle, in the case of which a needle body has a proximal needle section and a distal needle section, in which a piercing tip is arranged, wherein the needle body has a needle section, which is resilient against the piercing tip in response to a compressive stress, wherein the resilient needle section is arranged on the needle body in the area of an angled needle section, in which adjacent needle sections assume an angle of less than 180° with one another. Further, a hand-held device for repeated local puncturing of a human or an animal skin is provided.

9 Claims, 10 Drawing Sheets

(51) Int. Cl.
*A61B 5/151* (2006.01)
*A61D 7/00* (2006.01)
*A61M 5/178* (2006.01)
*A61B 17/20* (2006.01)

(56) References Cited

U.S. PATENT DOCUMENTS

| | | |
|---|---|---|
| 2007/0038181 A1 | 2/2007 | Melamud et al. |
| 2012/0029549 A1* | 2/2012 | Weston ............ A61M 37/0076 606/186 |
| 2012/0295549 A1 | 11/2012 | Slotznick |
| 2015/0142040 A1* | 5/2015 | Kawaura .......... A61B 17/06109 606/185 |
| 2017/0014194 A1* | 1/2017 | Duindam ................ A61B 5/065 |
| 2017/0202613 A1* | 7/2017 | Pellegrino ................ A61N 5/00 |

FOREIGN PATENT DOCUMENTS

| | | |
|---|---|---|
| EP | 1 958 659 | 8/2008 |
| EP | 2 149 388 | 2/2010 |
| EP | 2 682 146 | 1/2014 |

* cited by examiner

SKIN PIERCING TOOL FOR LOCALLY PUNCTURING A HUMAN OR AN ANIMAL SKIN AND HAND-HELD DEVICE

CROSS-REFERENCE TO RELATED APPLICATIONS

The present application claims priority under 35 U.S.C. § 119 to European Patent Application No. 15158066.9, filed Mar. 6, 2015, which is hereby incorporated by reference in its entirety.

The invention relates to a skin piercing tool for locally puncturing a human or an animal skin as well as to a hand-held device.

BACKGROUND

Skin piercing tools are used in hand-held devices for locally puncturing a human or an animal skin. Such hand-held devices can serve to introduce a substance via the skin, for example a dye in combination with permanent makeup or the design of a tattoo. However, medical or cosmetic substances can also be applied into the skin or through the skin by using such a hand-held device.

Skin piercing tools are known in the form of cannulas or solid needles.

Devices, which have a drive device, which repetitively provides a drive force for extending and retracting the skin piercing tool, are used as hand-held devices. The skin piercing tool can hereby be formed with a single needle or in the form of a needle group. In addition, needle plates for puncturing the skin are known.

A skin piercing tool, which has a plurality of hollow needles, which can bend flexibly, when pressure is applied to the respective tip of the hollow needle in response to piercing, is known from document US 2005/065483 A1. In one embodiment, the hollow needles have local apertures or openings in the wall, through which a liquid, which is to be introduced, can escape.

Further skin piercing tools are known from the following documents: EP 1 576 982 A1, US 2012/0295549 A1 and US 2007/038181 A1. The needles of the known piercing tools can be embodied as solid needles.

SUMMARY

It is an object to specify a skin piercing tool as well as a hand-held device for locally puncturing a human or an animal skin, by means of which an improved local puncturing of the skin is made possible, so as to optimize the substance introduction, for example.

To solve the object, a skin piercing tool for locally puncturing a human or an animal skin according to independent claim 1 is created. Claim 14 relates to a hand-held device for locally puncturing a human or an animal skin. Embodiments are the subject matter of dependent claims.

According to one aspect, a skin piercing tool for locally puncturing a human or an animal skin is provided, which has a piercing needle, wherein a needle body has a proximal needle section and a distal needle section, in which a piercing tip is arranged. The needle body has a needle section, which is resilient in response to a compressive stress against the piercing tip. The needle is formed as solid needle.

According to a further aspect, a hand-held device for repeated local puncturing of a human or an animal skin is creased, wherein the skin piercing tool is arranged on a needle module, which functionally couples to a drive module, by means of which a drive force for extending and retracting at least the piercing tip of the skin piercing tool is provided repetitively.

When the skin piercing tool is pushed with its piercing tip against a surface, which puts up a resistance against the pushing, the piercing needle yields resiliently. In one embodiment, the distal needle section can thus perform a tilting, folding or pivoting movement with reference to the longitudinal direction of the needle body.

The resilient needle section can be arranged on the needle body between the proximal and the distal needle section.

The resilient needle section is arranged on the needle body in the area of an angled needle section, in which adjacent needle sections assume an angle of less than 180° with one another.

The needle sections adjacent to the resilient needle section can be identical or different with regard to the design thereof. For example, the adjacent needle sections can be embodied as straight or as curved needle sections. In one embodiment, the elastic spring motion can have the effect that the adjacent needle sections are moved towards one another.

The resilient needle section can be arranged on the needle body in the region of a curved needle section. In combination with a curved resilient needle section, the needle sections adjacent thereto can also be straight or curved, wherein the adjacent needle sections can have the same shape or different shapes.

A further resilient needle section can be arranged on the needle body in the area of a loop needle section. A closed loop can be formed. The loop needle section can have a circularity.

The distal needle section can be placed at an incline to the longitudinal direction of the needle body. In the case of this embodiment or other embodiments, the longitudinal direction of the needle body can coincide with a piercing or application direction in case of application. The distal needle section can be formed as straight needle section, in particular also starting at the piercing tip. In the alternative, the distal needle section can have a curved form, for example also starting at the piercing tip.

A needle section adjoining the distal needle section can be placed at an incline to the longitudinal direction of the needle body. If the distal needle section is also placed at an incline to the longitudinal direction of the needle body, the inclination of the adjoining needle section can be formed with an opposite angle, wherein the inclinations with reference to the longitudinal direction of the needle body can be embodied with the same angle or with different angles. In one embodiment, the distal needle section and the adjoining needle section can be arranged in accordance with a horizontal V-position, wherein the resilient needle section can be formed between the adjacent needle sections in one embodiment.

For the resilient needle section, adjacent needle sections can be adapted to carry out a scissor leg movement in response to being resilient.

The resilient needle section can be formed with a material thinning and/or thickening with regard to a needle section adjacent thereto. The thinning and/or the thickening can be formed with the help of a profiling on the surface side of the needle body in the area of the resilient needle section.

The needle body can have a further needle section, which is resilient against the piercing tip in response to a compressive stress. The resilient needle section or sections can be adapted to be resilient as reaction to a compressive force, which is directed substantially parallel to the longitudinal direction of the needle body. The resilient needle sections can be formed in the same or in a different shape, for example with regard to a spring constant and/or with regard to the provided material shape, for example the cross sectional shape.

A further piercing needle can form a piercing needle group with the piercing needle. The piercing needles of the piercing needle group can be embodied identically or different.

The respective resilient needle sections of the piercing needle and of the further piercing needle can be arranged so as to adjoin one another.

The respective resilient needle sections of the piercing needle and of the further piercing needle can be arranged so as to be offset relative to one another in longitudinal direction of the piercing needle group.

A skin piercing tool can be arranged so as to be located next to one another in a plane. In the alternative, the plurality of the piercing needles of the piercing needle group can be embodied as a non-flat bundle of needles.

As an alternative to the hand-held device for repeated puncturing of a human or an animal skin, a hand-held device comprising the skin-piercing tool can be provided as hand-held individual piercing device. Such a hand-held device can be embodied without the drive module, by means of which the drive force is provided so as to repeat automatically, for example comprising a repetition frequency of at least 50 Hz. Such hand-held devices as such are disclosed in the following documents: EP 1 872 823 A1, EP 1 958 659 A1, EP 2 149 388 A1 and EP 2 682 146 A1.

DESCRIPTION OF EXEMPLARY EMBODIMENTS

Further exemplary embodiments will be explained below with reference to figures of a drawing.

Figure 1:
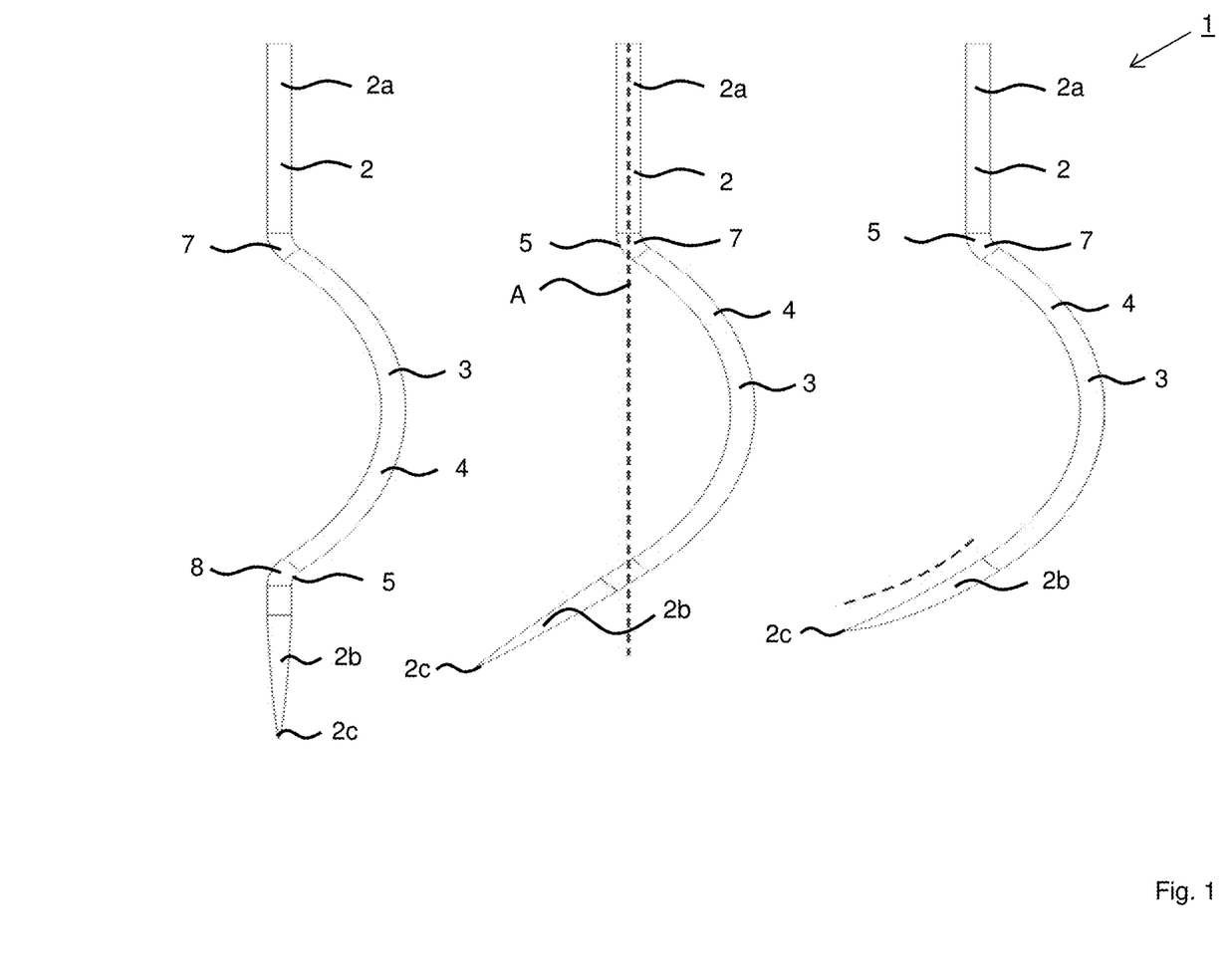
FIG. 1 shows a schematic illustration of a piercing needle comprising a pronounced curved needle section.
Figure 2:
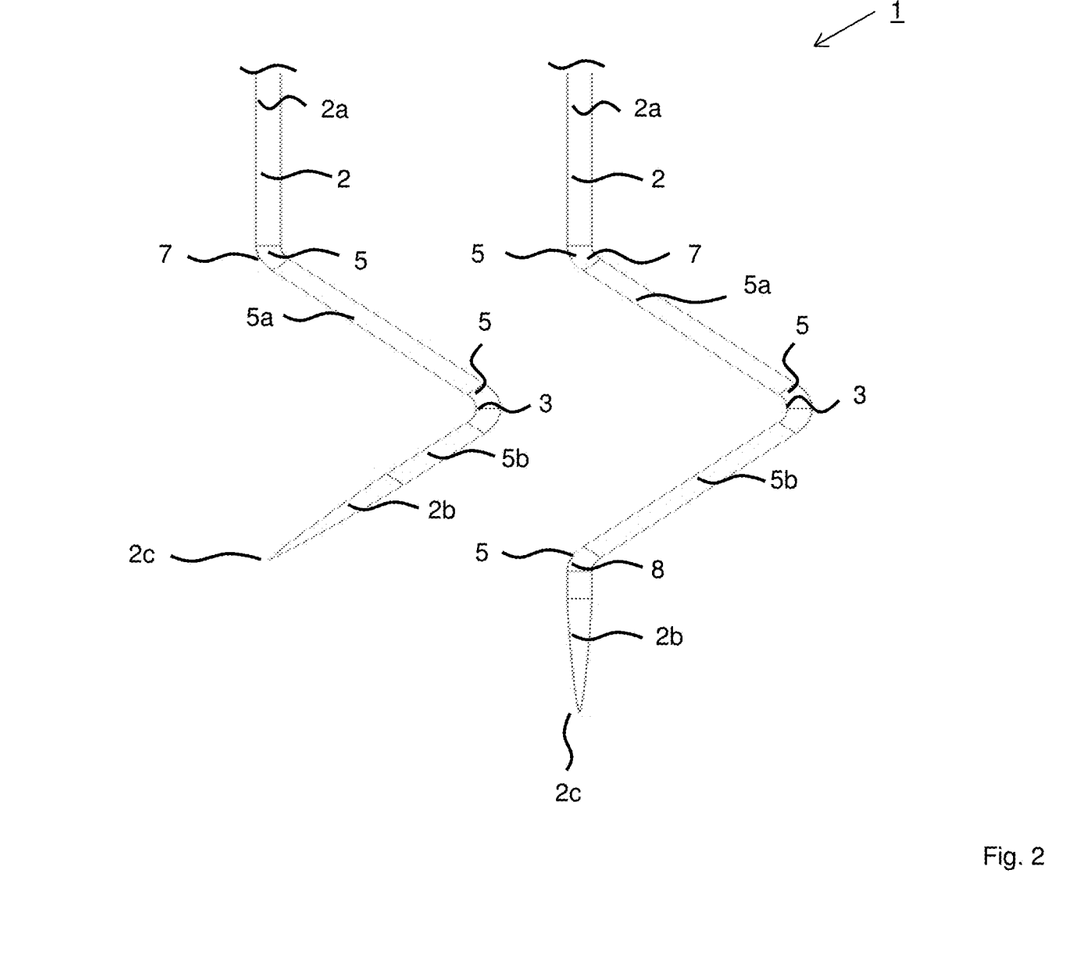
FIG. 2 shows schematic illustrations of piercing needles comprising an angled needle section.
Figure 3:
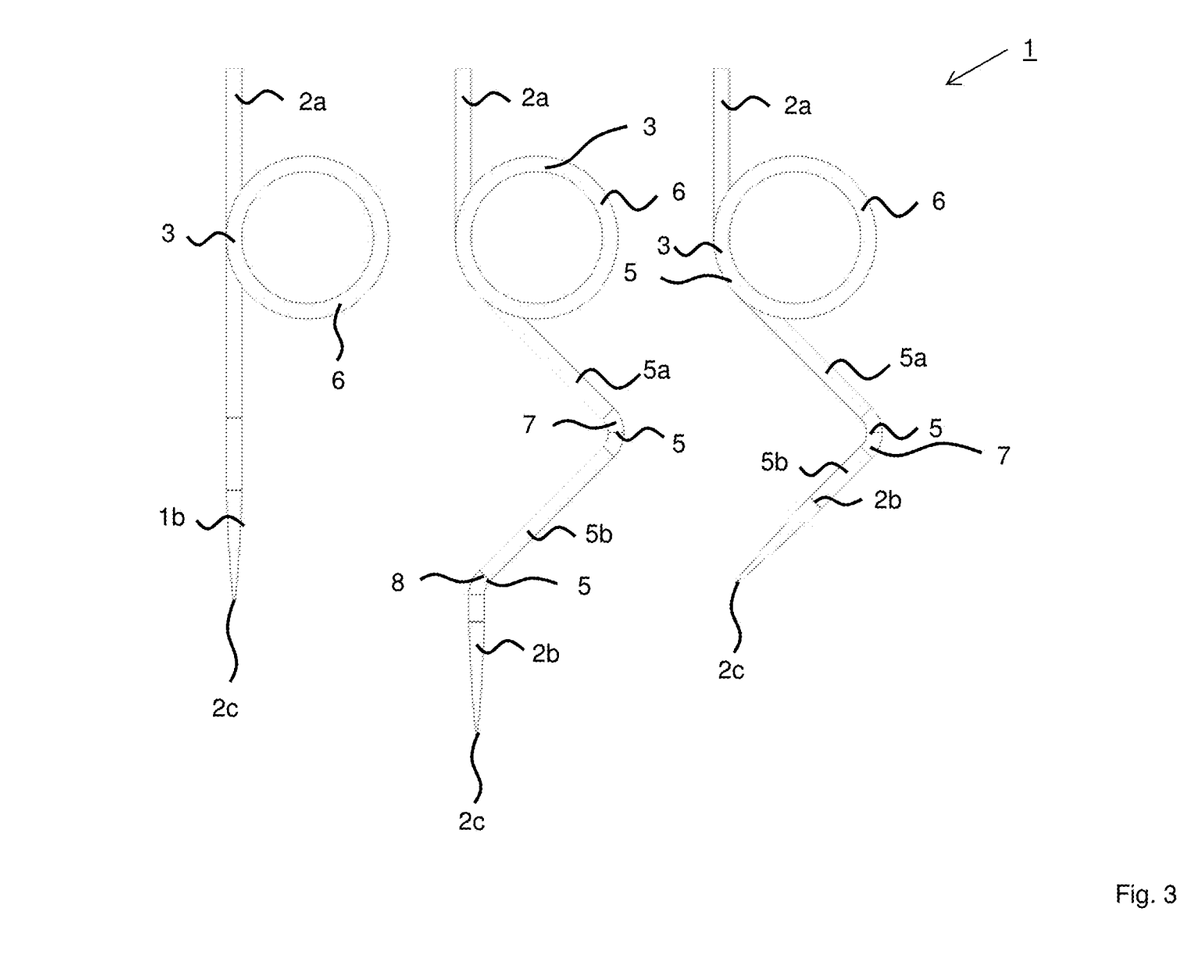
FIG. 3 shows schematic illustrations of piercing needles comprising a loop needle section.

FIGS. 1 to 3 show embodiments for a single piercing needle 1, wherein provision is made on the needle body 2 for a resilient needle section 3. FIG. 1 shows an embodiment, in the case of which the needle body 2 has a curved needle section 4.

The different embodiments (see also FIGS. 2 and 3 are provided with one or a plurality of angled areas 5, to which adjacent straight needle sections 5a, 5b connect. In the alternative, one or a both adjacent sections adjacent to the angled area can be curved. In the case of the straight sections, the latter assume an angle of less than 180°. If one or two adjacent sections are curved, the straight section and the tangent to the curved section or the tangents to the two curved sections, which start at the angled section, assume an angle of less than 180°.

FIG. 3 shows embodiments, in the case of which a loop needle section 6 forms a resilient needle section on the needle body 3. As an alternative to the shown embodiment, the position of the loop needle section 6 can be interchanged with angled area 5.

On the needle body 2, the individual piercing needles 1 have a proximal and a distal needle section 2a, 2b, wherein a piercing tip 2c is arranged on the distal needle section. The proximal needle section 2a can be formed as needle shaft, which can be used to fasten the piercing needle 1 to a hand-held device for locally puncturing a skin.

FIG. 1 shows a longitudinal direction of the needle body 2 in a schematic manner by means of a dashed line A.

In the case of the different embodiments, at least one further resilient needle section 7, 8 can be formed. In the alternative, the piercing needle 1 can also be embodied so as to be substantially non-resilient in this needle section, so that a resilience occurs only in the region of the resilient needle section 3 when pressure is applied to the piercing tip 1c.

Figure 4:
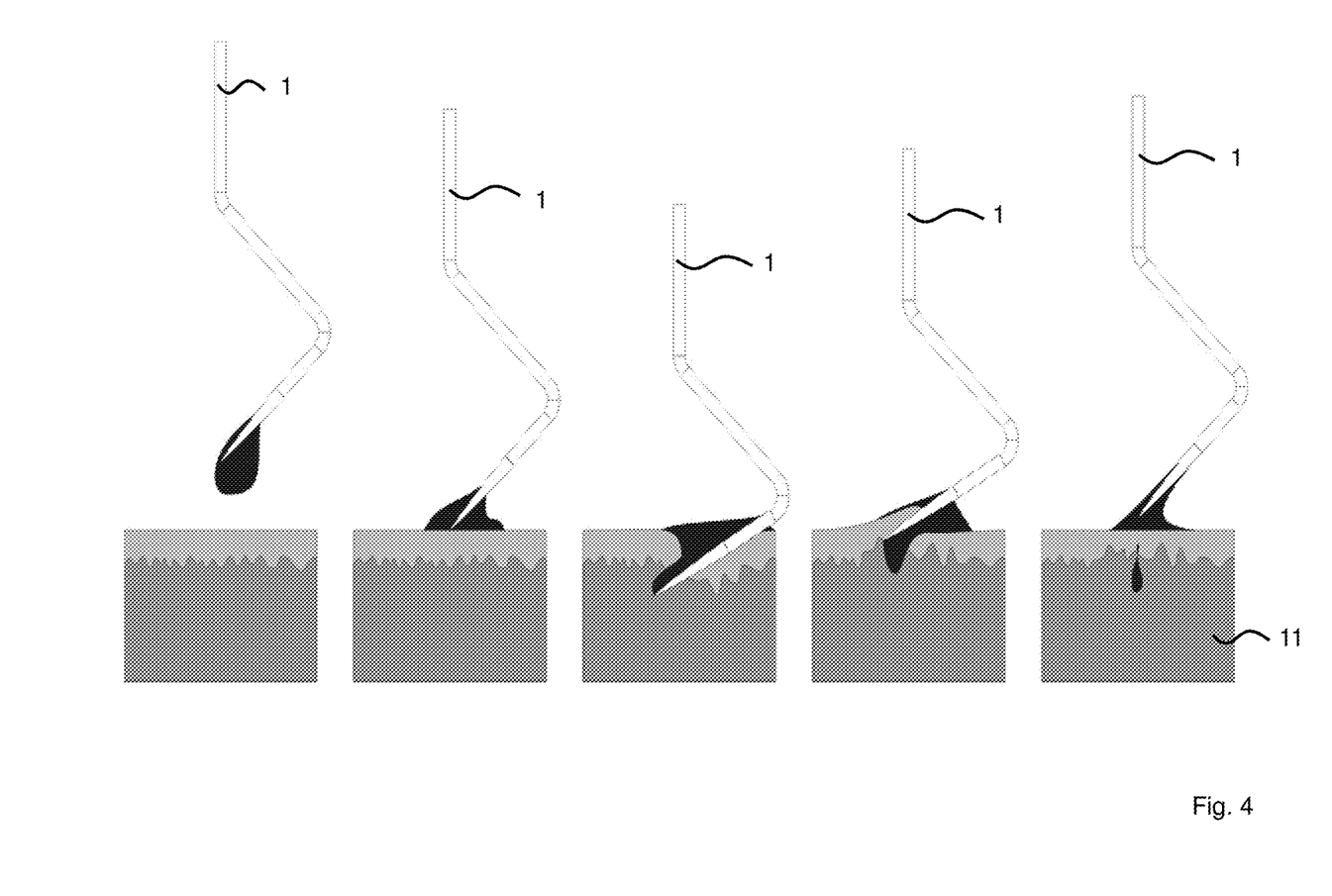
FIG. 4 shows a schematic illustration relating to the mode of operation of an embodiment of a piercing needle.
Figure 5:
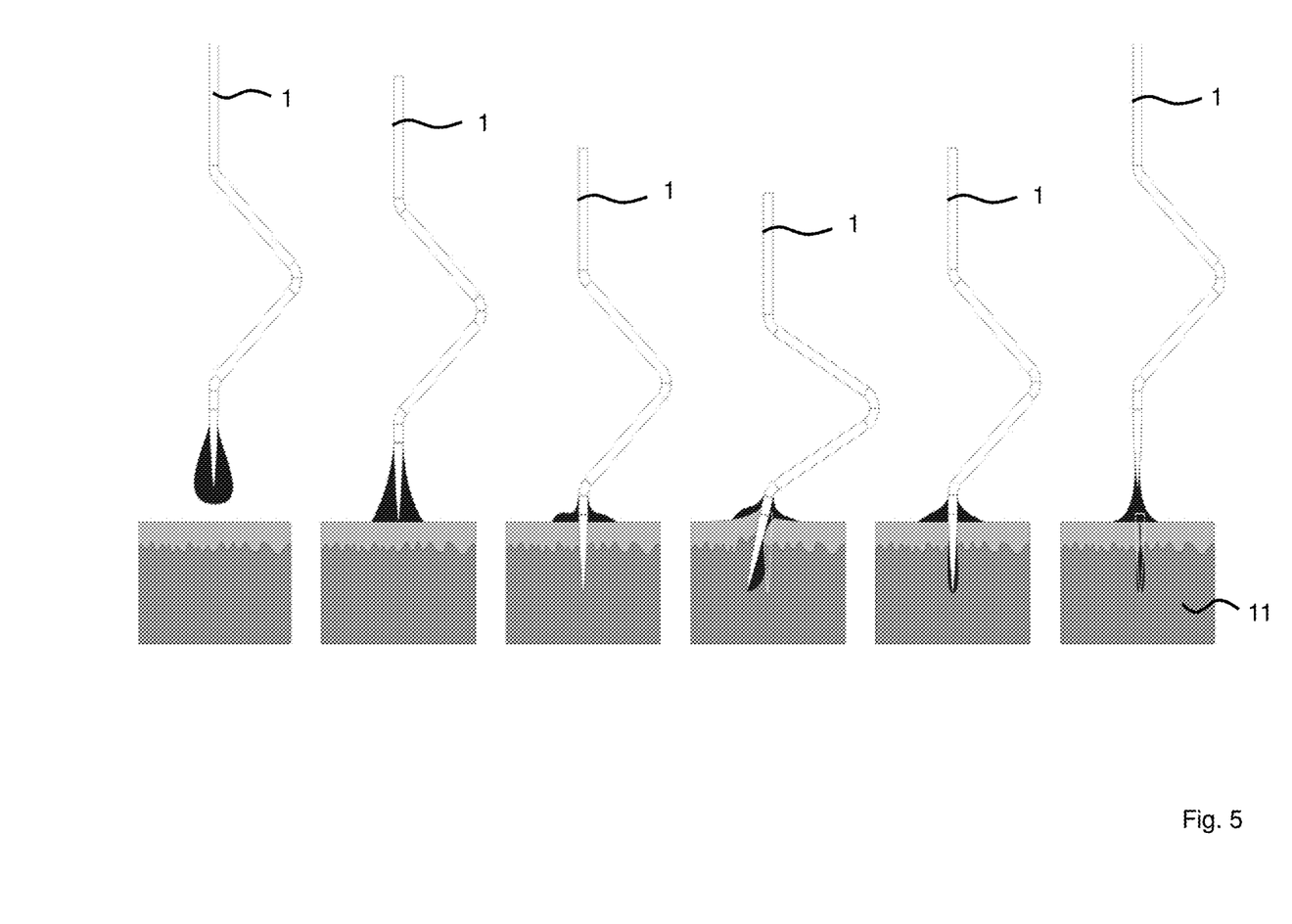
FIG. 5 shows a schematic illustration relating to the mode of operation of a further embodiment of a piercing needle.

When using the piercing needle 1, the provision of the resilient needle section or sections 3, 5, 7, 8 leads to the tilting or pivoting of at least the distal needle section 2b, when pressure is applied to the piercing tip 1c in response to puncturing the skin. This is shown schematically in FIGS. 4 and 5. The substance introduction into a skin 11, for which a section is shown in cross section in FIGS. 4 and 5, can be improved in this manner.

Figure 6:
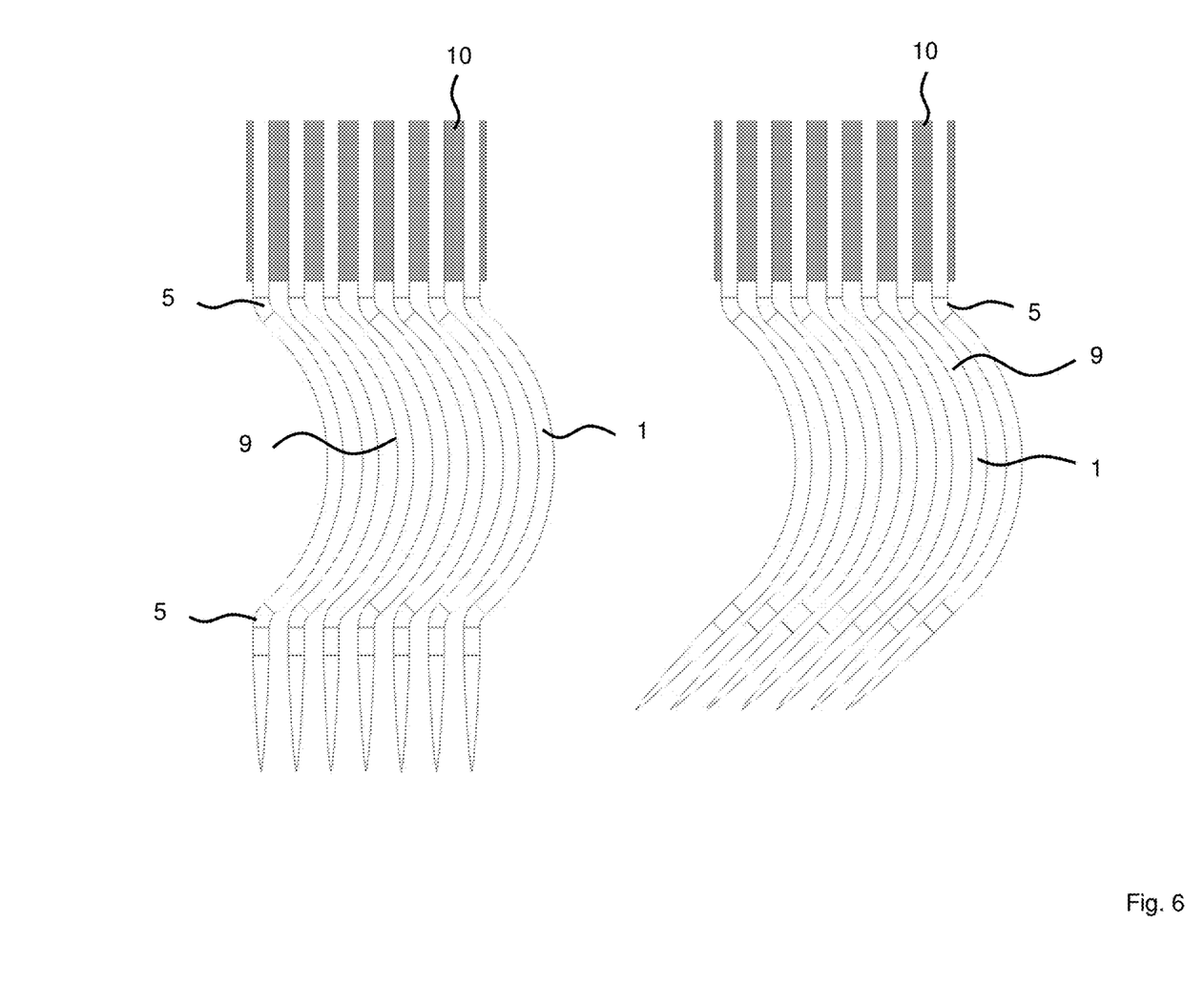
FIG. 6 shows schematic illustrations of piercing needle groups comprising piercing needles with curved needle section.
Figure 7:
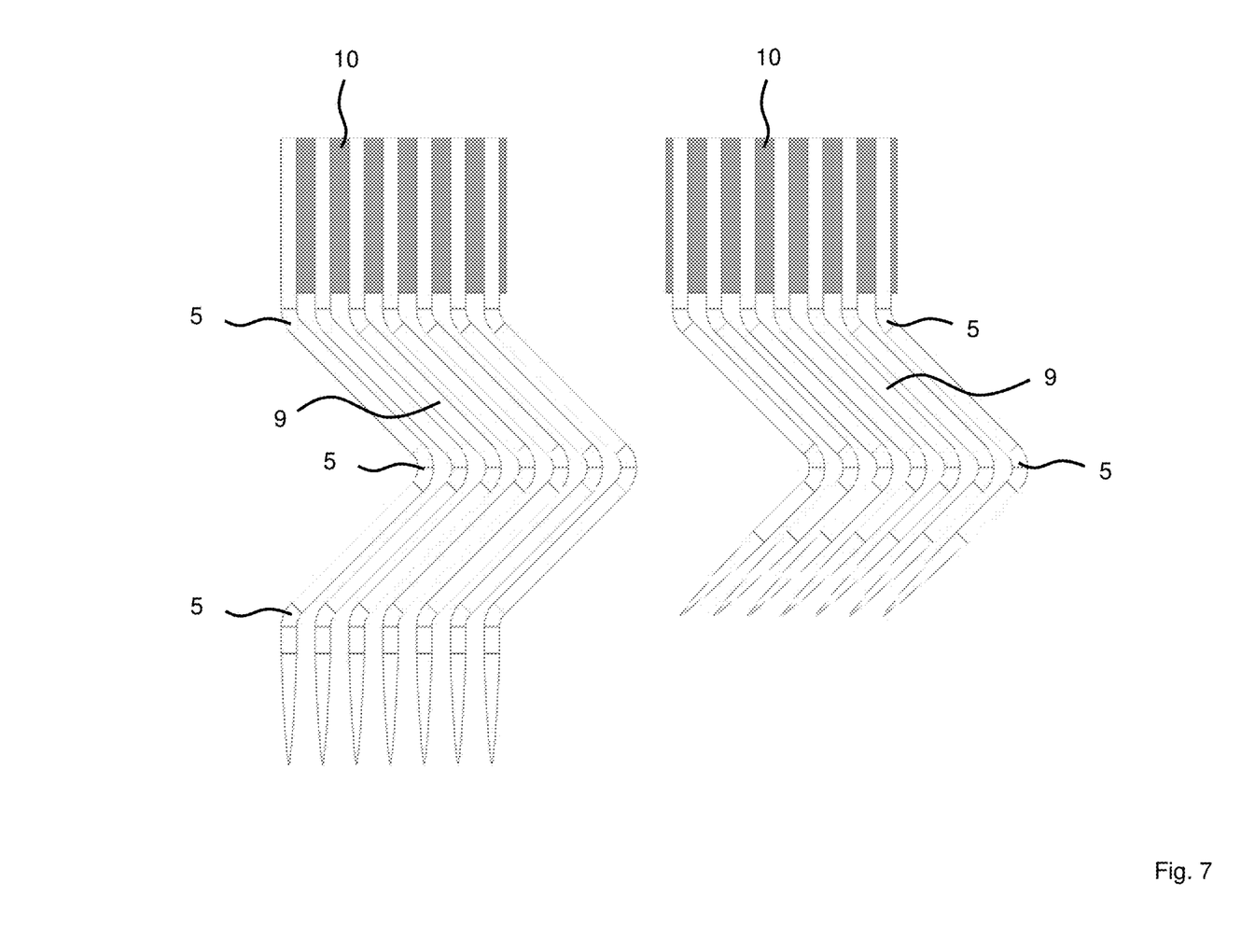
FIG. 7 shows schematic illustrations of piercing needle groups comprising piercing needles with angled needle section.

FIGS. 6 and 7 show schematic illustrations of piercing needle groups 9, in the case of which a plurality of the piercing needles 1 shown in FIGS. 1 to 3, which are arranged on a needle holder 10, form a skin piercing tool.

Figure 8:
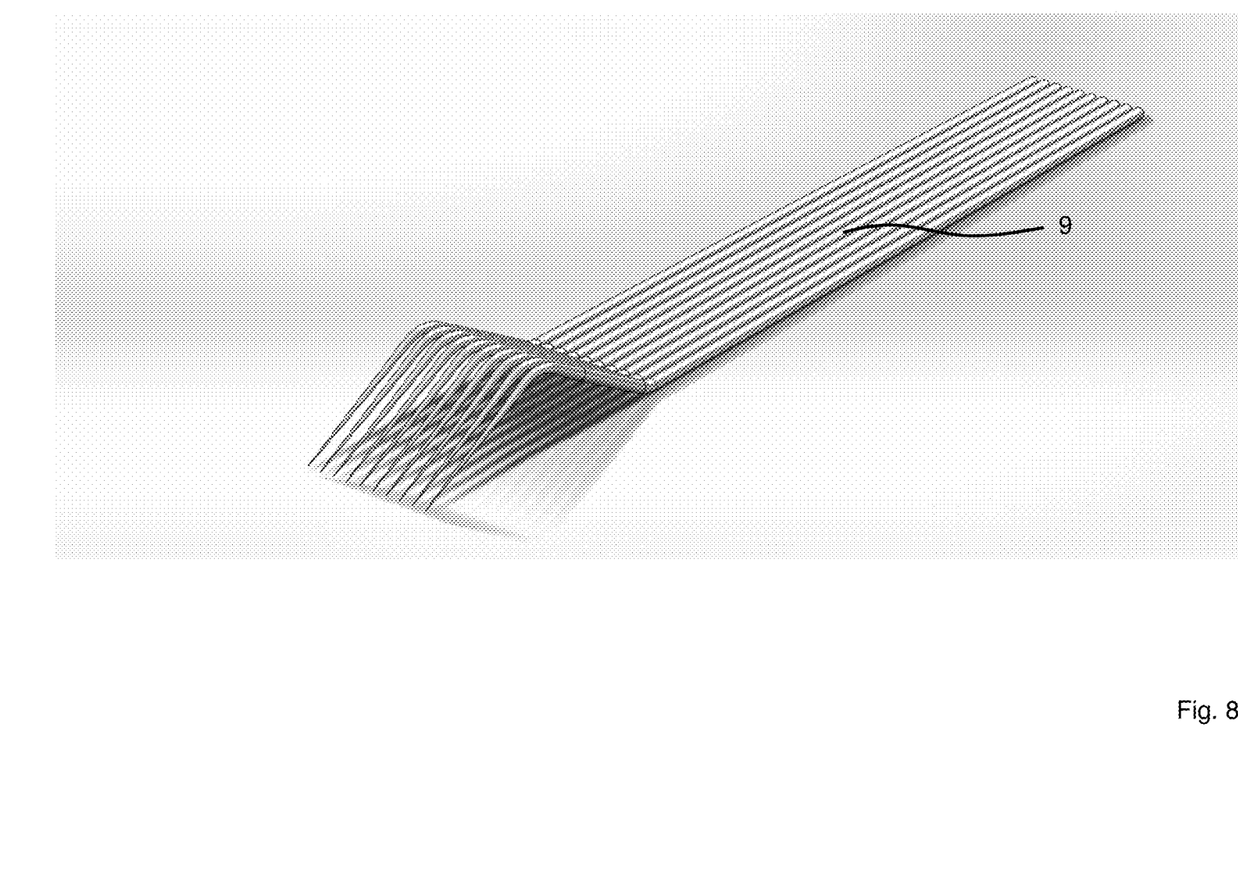
FIG. 8 shows a perspective illustration of a piercing needle group.
Figure 9:
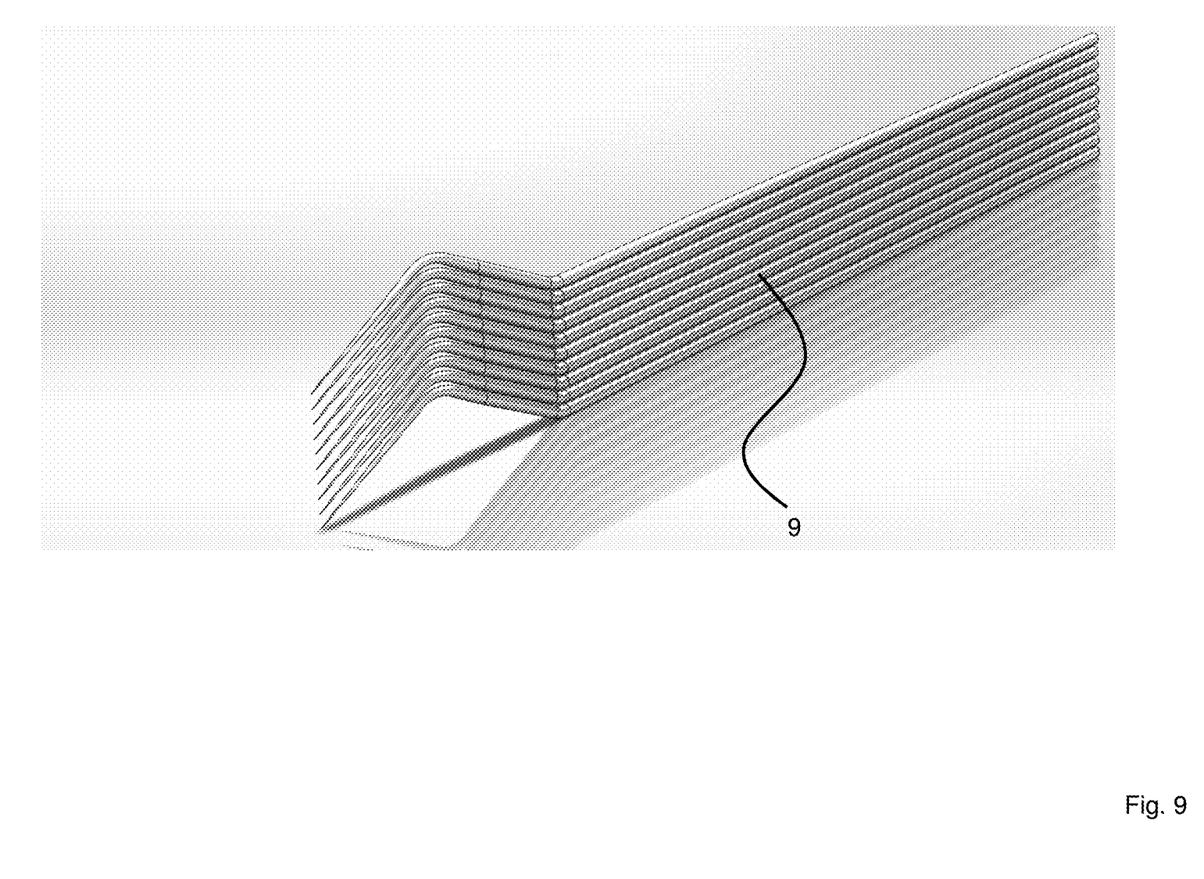
FIG. 9 shows a perspective illustration of a different piercing needle group.

FIGS. 8 and 9 in each case show a perspective illustration of a piercing needle group 9, in the case of which proximal needle sections 2a of a plurality of piercing needles are arranged next to one another in a plane. The shown embodiments of the piercing needle 1 are embodied as solid needle.

Figure 10:
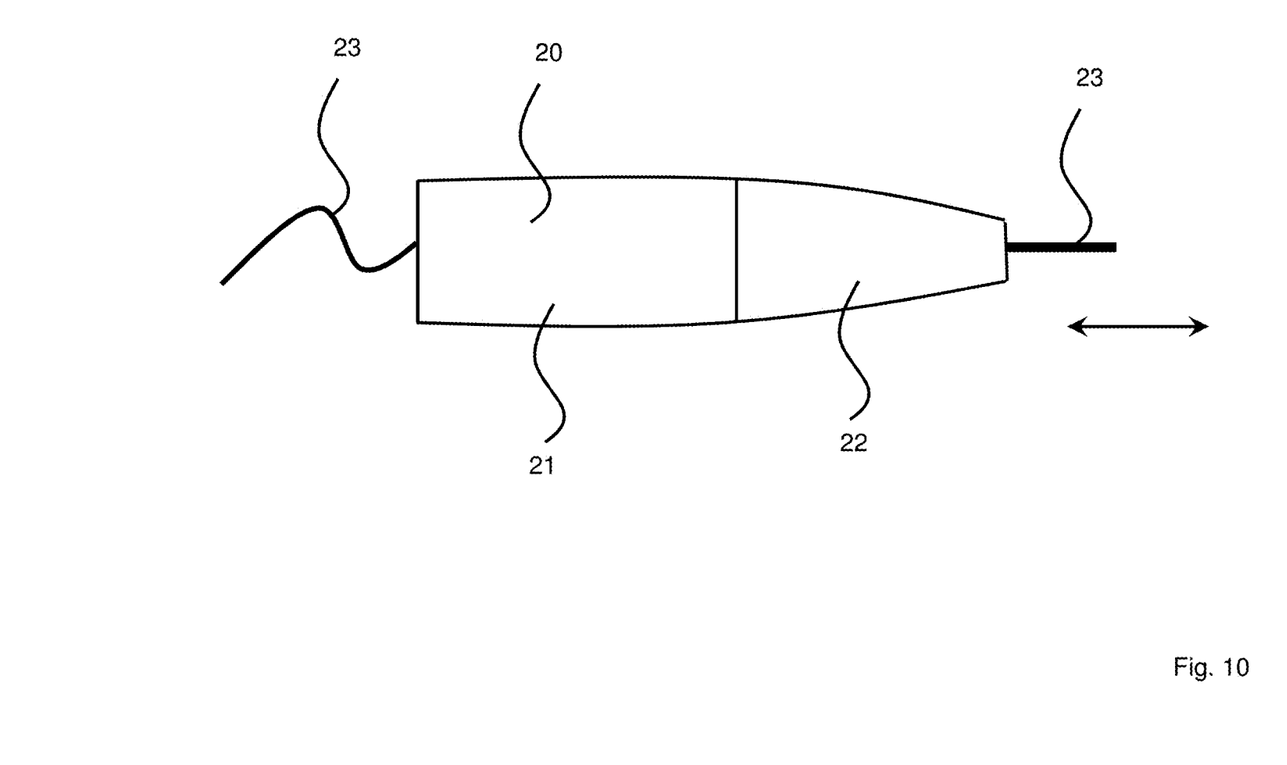
FIG. 10 shows a schematic illustration of a hand-held device for repeatedly puncturing a skin.

FIG. 10 shows a schematic illustration of a hand-held device 20 for repeatedly puncturing a skin comprising a drive module 21, to which a needle module 22 couples functionally. A skin piercing tool 23 in one of the embodiments described herein is arranged on the needle module 22. The drive module can be connected to an electrical power supply via a cable 24, for example via a control device (not illustrated). Provision can also be made for a cable-free battery operation.

The features disclosed in the description above, the claims as well as the drawing can be significant for the realization of the different embodiments, both alone as well as in any combination.

The invention claimed is:

1. A skin piercing tool for locally puncturing a human or an animal skin, comprising a piercing needle, which is embodied as solid needle, wherein a needle body of the piercing needle has needle sections including at least a proximal needle section and a at least a distal needle section, in which a piercing tip is arranged, wherein the body of the piercing needle has at least two resilient sections, each resilient section having a bend and being flexible and resilient in response to a compressive stress against the piercing tip, the bend of at least one of the at least two resilient sections being oriented in a different direction from the bend of at least one of the other at least two resilient sections, wherein the proximal needle section and at least one of the at least two resilient sections assume an angle of less than 180 degrees with respect to each other, and additionally comprising at least one further piercing needle, which forms a piercing needle group with the piercing needle.

2. The skin piercing tool according to claim 1, characterized in that the at least two resilient sections are arranged on the body of the piercing needle between the proximal needle section and the distal needle section.

3. The skin piercing tool according to claim 1, characterized in that the distal needle section is placed at an incline to a longitudinal direction of the body of the piercing needle.

4. The skin piercing tool according to claim 1, characterized in that one of the at least two resilient sections adjoining the distal needle section is placed at an incline to a longitudinal direction of the body of the piercing needle.

5. The skin piercing tool according to claim 1, characterized in that needle sections adjacent to the at least two resilient needle sections are adapted to carry out a folding or pivoting movement due to the resilience of the at least two resilient sections.

6. The skin piercing tool according to claim 1, characterized in that the at least two resilient needle sections are formed with at least one of a thinner material and a thicker material than either needle section adjacent thereto.

7. The skin piercing tool according to claim 1, characterized in that the at least two resilient sections of the piercing needle and at least two resilient sections of the at least one further piercing needle are arranged so as to be located next to one another.

8. The skin piercing tool according to claim 1, characterized in that the at least two resilient sections of the piercing needle and at least two resilient sections of the at least one further piercing needle are arranged so as to be offset relative to one another in a longitudinal direction of the piercing needle group.

9. The skin piercing tool according to claim 1, characterized in that the piercing needle and the further piercing needle are arranged so as to be located next to one another in a plane.

\* \* \* \* \*